(12) United States Patent
Roggen

(10) Patent No.: US 7,226,770 B2
(45) Date of Patent: Jun. 5, 2007

(54) LIPOLYTIC ENZYME VARIANT

(75) Inventor: Erwin Ludo Roggen, Lyngby (DK)

(73) Assignee: Novozymes A/s, Bagsvaerd (DK)

( * ) Notice: Subject to any disclaimer, the term of this patent is extended or adjusted under 35 U.S.C. 154(b) by 218 days.

(21) Appl. No.: 10/258,783

(22) PCT Filed: Apr. 30, 2001

(86) PCT No.: PCT/DK01/00286

§ 371 (c)(1),
(2), (4) Date: Oct. 28, 2002

(87) PCT Pub. No.: WO01/83770

PCT Pub. Date: Nov. 8, 2001

(65) Prior Publication Data

US 2003/0144165 A1    Jul. 31, 2003

Related U.S. Application Data

(60) Provisional application No. 60/277,817, filed on Mar. 21, 2001, provisional application No. 60/203,345, filed on May 10, 2000.

(51) Int. Cl.
*C12N 9/16* (2006.01)
*C12N 9/20* (2006.01)

(52) U.S. Cl. ................ 435/196; 435/198; 435/252.3; 435/320.1; 435/911; 536/23.2

(58) Field of Classification Search ............... 435/198, 435/252.3, 320.1, 471, 911, 196; 536/23.2; 510/305, 392, 226
See application file for complete search history.

(56) References Cited

U.S. PATENT DOCUMENTS 5,869,438 A * 2/1999 Svendsen et al. ........... 510/226
6,624,129 B1 * 9/2003 Borch et al. ................ 510/226

FOREIGN PATENT DOCUMENTS

| | | |
|---|---|---|
| EP | 0 305 216 | 3/1989 |
| WO | WO 92/05249 | 4/1992 |
| WO | WO 97/04078 | 2/1997 |

* cited by examiner

Primary Examiner—Tekchand Saidha
(74) Attorney, Agent, or Firm—Jason I. Garbell

(57) ABSTRACT

The properties of a fungal lipolytic enzyme can be altered by substituting amino acid residues corresponding to certain specified amino acid residues in the *T. lanuginosus* lipase. The altered property may be, e.g., an increased thermostability, an altered pH dependence, or an altered substrate specificity.

23 Claims, No Drawings

SEQUENCE LISTING

```
<160> NUMBER OF SEQ ID NOS: 1

<210> SEQ ID NO 1
<211> LENGTH: 269
<212> TYPE: PRT
<213> ORGANISM: Thermomyces lanuginosus

<400> SEQUENCE: 1

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
```

-continued

```
                    115                 120                 125
Glu Asp Ala Val Arg Glu His Pro Asp Tyr Arg Val Val Phe Thr Gly
        130                 135                 140
His Ser Leu Gly Gly Ala Leu Ala Thr Val Ala Gly Ala Asp Leu Arg
145                 150                 155                 160
Gly Asn Gly Tyr Asp Ile Asp Val Phe Ser Tyr Gly Ala Pro Arg Val
                165                 170                 175
Gly Asn Arg Ala Phe Ala Glu Phe Leu Thr Val Gln Thr Gly Gly Thr
            180                 185                 190
Leu Tyr Arg Ile Thr His Thr Asn Asp Ile Val Pro Arg Leu Pro Pro
        195                 200                 205
Arg Glu Phe Gly Tyr Ser His Ser Ser Pro Glu Tyr Trp Ile Lys Ser
    210                 215                 220
Gly Thr Leu Val Pro Val Thr Arg Asn Asp Ile Val Lys Ile Glu Gly
225                 230                 235                 240
Ile Asp Ala Thr Gly Gly Asn Asn Gln Pro Asn Ile Pro Asp Ile Pro
                245                 250                 255
Ala His Leu Trp Tyr Phe Gly Leu Ile Gly Thr Cys Leu
        260                 265
```

US 7,226,770 B2

LIPOLYTIC ENZYME VARIANT

CROSS-REFERENCE TO RELATED APPLICATIONS

This application is a 35 U.S.C. 371 national application of PCT/DK01/00286 filed Apr. 30, 2001 (the international application was published under PCT Article 21(2) in English) and claims, under 35 U.S.C. 119, priority or the benefit of Danish application nos. PA 2000 00707, filed Apr. 28, 2000 and PA 2001 00327, filed Feb. 28, 2001 and U.S. provisional application nos. 60/277,817, filed Mar. 21, 2001, and 60/203,345, filed May 10, 2000, the contents of which are fully incorporated herein by reference.

FIELD OF THE INVENTION

The present invention relates to variants of fungal lipolytic enzymes, particularly variants with altered properties, and to methods of producing such variants.

BACKGROUND OF THE INVENTION

It is known to use fungal lipolytic enzymes, e.g. the lipase from *Thermomyces lanuginosus* (synonym *Humicola lanuginosa*), for various industrial purposes, such as addition to detergents and in baking.

WO 92/05249, WO 9219726, WO 97/07202 and WO 0032758 disclose variants of the *T. lanuginosus* (*H. lanuginosa*) lipase having altered properties.

SUMMARY OF THE INVENTION

The inventors have found that the properties of a fungal lipolytic enzyme can be altered by substituting certain amino acid residues.

Accordingly, the invention provides a variant of a parent fungal lipolytic enzyme, which variant comprises substitution of one or more specified amino acid residues. The invention also provides a method of producing a lipolytic enzyme variant comprising:

a) selecting a parent fungal lipolytic enzyme, b) in the parent lipolytic enzyme substituting at least one specified amino acid residue, c) optionally, substituting one or more amino acids other than b), d) preparing the variant resulting from steps a)–c), e) testing a property of the variant, f) selecting a variant wherein the property is altered compared to the parent lipolytic enzyme, and g) producing the selected variant.

The specified amino acid residue corresponds to any of the following amino acids in SEQ ID NO: 1:

Q15, Y16, A18, A19, A20, N25, N26, E43, V44, K46, A47, A49, L52, Y53, S54, G65, L67, A68, L69, T72, K74, L75, V77, S79, R81, S83, S85, W89, D96, L97, K98, E99, G106, C107, R108, G109, T123, L124, K127, E129, A131, V132, Y138, V140, L147, A150, T153, Y164, D165, D167, S170, Y171, G172, A173, P174, R175, V176, G177, R179, A182, Y194, H198, N200, P207, P208, R209, G212, S214, H215, S216, S217, P218, E219, Y220, K223, S224, D234, I235, K237, I238, D242 to A243, P250, P253, D254, I255, P256, Y261.

DETAILED DESCRIPTION OF THE INVENTION

Parent Lipolytic Enzyme

The lipolytic to be used in the present invention is classified in EC 3.1.1 Carboxylic Ester Hydrolases according to Enzyme Nomenclature. The substrate specificity may include activities such as EC 3.1.1.26 triacylglycerol lipase, EC 3.1.1.4 phospholipase A2 EC 3.1.1.5 lysophospholipase, EC 3.1.1.32 phospholipase A1, EC 3.1.1.73 feruloyl esterase.

The parent lipolytic enzyme is fungal and has an amino acid sequence that can be aligned with SEQ ID NO: 1 which is the amino acid sequence shown in positions 1–269 of SEQ ID NO: 2 of U.S. Pat. No. 5,869,438 for the lipase from *Thermomyces lanuginosus* (synonym *Humicola lanuginosa*), described in EP 258 068 and EP 305 216. The parent lipolytic enzyme may particularly have an amino acid sequence with at least 50% homology with SEQ ID NO: 1. In addition to the lipase from *T. lanuginosus*, other examples are a lipase from *Penicillium camembertii* (P25234), lipase/phospholipase from *Fusarium oxysporum* (EP 130064, WO 98/26057), lipase from *F. heterosporum* (R87979), lysophospholipase from *Aspergillus foetidus* (W33009), phospholipase A1 from *A. oryzae* (JP-A 10–155493), lipase from *A. oryzae* (D85895), lipase/ferulic acid esterase from *A. niger* (Y09330), lipase/ferulic acid esterase from *A. tubingensis* (Y09331), lipase from *A. tubingensis* (WO 98/45453), lysophospholipase from *A. niger* (WO 98/31790), lipase from *F. solanii* having an isoelectric point of 6.9 and an apparent molecular weight of 30 kDa (WO 96/18729).

Other examples are the Zygomycetes family of lipases comprising lipases having at least 50% homology with the lipase of *Rhizomucor miehei* (P19515) having the sequence shown in SEQ ID NO: 2. This family also includes the lipases from *Absidia reflexa, A. sporophora, A. corymbifera, A. blakesleeana, A. griseola* (all described in WO 96/13578 and WO 97/27276) and *Rhizopus oryzae* (P21811). Numbers in parentheses indicate publication or accession to the EMBL, GenBank, GeneSeqp or Swiss-Prot databases.

Lipolytic Enzyme Variants

The lipolytic enzyme variant of the invention comprises one or more substitutions of the specified amino acid residues. The total number of such substitutions is typically not more than 10, e.g. one, two, three, four, five or six of said substitutions.

In addition, the lipolytic enzyme variant of the invention may optionally include other modifications of the parent enzyme, typically not more than 10, e.g. not more than 5 such modifications.

The variant generally has a homology with the parent lipolytic enzyme of at least 80%, e.g. at least 85%, typically at least 90% or at least 95%.

Specific Substitutions

The variant may comprise substitutions corresponding to one or more of the following in the *T. lanuginosus* lipase (SEQ ID NO: 1) with the proviso that the amino acid of the parent enzyme is substituted with another amino acid:

Q15 to A, C, D, E, F, G, H, I, K, L, M, N, P, Q, R, S, T, V, W, Y;

Y16 to A, C, D, E, F, G, H, I, K, L, M, N, P, Q, R, S, T, V, W, Y;

A18 to A, C, D, E, F, G, H, I, K, L, M, N, P, Q, R, S, T, V, W, Y;

A19 to A, C, D, E, F, G, H, I, K, L, M, N, P, Q, R, S, T, V, W, Y;
A20 to A, C, D, E, F, G, H, I, K, L, M, N, P, Q, R, S, T, V, W, Y;
N25 to A, C, D, E, F, G, H, I, K, L, M, N, P, Q, R, S, T, V, W, Y;
N26 to A, C, D, E, F, G, H, I, K, L, M, N, P, Q, R, S, T, V, W, Y;
E43 to A, C, D, E, F, G, H, I, K, L, M, N, P, Q, R, S, T, V, W, Y;
V44 to A, C, D, E, F, G, H, I, K, L, M, N, P, Q, R, S, T, V, W, Y;
K46 to A, C, D, E, F, G, H, I, K, L, M, N, P, Q, R, S, T, V, W, Y;
A47 to A, C, D, E, F, G, H, I, K, L, M, N, P, Q, R, S, T, V, W, Y;
A49 to A, C, D, E, F, G, H, I, K, L, M, N, P, Q, R, S, T, V, W, Y;
L52 to A, C, D, E, F, G, H, I, K, L, M, N, P, Q, R, S, T, V, W, Y;
Y53 to A, C, D, E, F, G, H, I, K, L, M, N, P, Q, R, S, T, V, W, Y;
S54 to A, C, D, E, F, G, H, I, K, L, M, N, P, Q, R, S, T, V, W, Y;
G65 to A, C, D, E, F, G, H, I, K, L, M, N, P, Q, R, S, T, V, W, Y;
L67 to A, C, D, E, F, G, H, I, K, L, M, N, P, Q, R, S, T, V, W, Y;
A68 to A, C, D, E, F, G, H, I, K, L, M, N, P, Q, R, S, T, V, W, Y;
L69 to A, C, D, E, F, G, H, I, K, L, M, N, P, Q, R, S, T, V, W, Y;
T72 to A, C, D, E, F, G, H, I, K, L, M, N, P, Q, R, S, T, V, W, Y;
K74 to A, C, D, E, F, G, H, I, K, L, M, N, P, Q, R, S, T, V, W, Y;
L75 to A, C, D, E, F, G, H, I, K, L, M, N, P, Q, R, S, T, V, W, Y;
V77 to A, C, D, E, F, G, H, I, K, L, M, N, P, Q, R, S, T, V, W, Y;
S79 to A, C, D, E, F, G, H, I, K, L, M, N, P, Q, R, S, T, V, W, Y;
R81 to A, C, D, E, F, G, H, I, K, L, M, N, P, Q, R, S, T, V, W, Y;
S83 to A, C, D, E, F, G, H, I, K, L, M, N, P, Q, R, S, T, V, W, Y;
S85 to A, C, D, E, F, G, H, I, K, L, M, N, P, Q, R, S, T, V, W, Y;
W89 to A, C, D, E, F, G, H, I, K, L, M, N, P, Q, R, S, T, V, W, Y;
D96 to A, C, D, E, F, G, H, I, K, L, M, N, P, Q, R, S, T, V, W, Y;
L97 to A, C, D, E, F, G, H, I, K, L, M, N, P, Q, R, S, T, V, W, Y;
K98 to A, C, D, E, F, G, H, I, K, L, M, N, P, Q, R, S, T, V, W, Y;
E99 to A, C, D, E, F, G, H, I, K, L, M, N, P, Q, R, S, T, V, W, Y;
G106 to A, C, D, E, F, G, H, I, K, L, M, N, P, Q, R, S, T, V, W, Y;
C107 to A, C, D, E, F, G, H, I, K, L, M, N, P, Q, R, S, T, V, W, Y;
R108 to A, C, D, E, F, G, H, I, K, L, M, N, P, Q, R, S, T, V, W, Y;
G109 to A, C, D, E, F, G, H, I, K, L, M, N, P, Q, R, S, T, V, W, Y;
T123 to A, C, D, E, F, G, H, I, K, L, M, N, P, Q, R, S, T, V, W, Y;
L124 to A, C, D, E, F, G, H, I, K, L, M, N, P, Q, R, S, T, V, W, Y;
K127 to A, C, D, E, F, G, H, I, K, L, M, N, P, Q, R, S, T, V, W, Y;
E129 to A, C, D, E, F, G, H, I, K, L, M, N, P, Q, R, S, T, V, W, Y;
A131 to A, C, D, E, F, G, H, I, K, L, M, N, P, Q, R, S, T, V, W, Y;
V132 to A, C, D, E, F, G, H, I, K, L, M, N, P, Q, R, S, T, V, W, Y;
Y138 to A, C, D, E, F, G, H, I, K, L, M, N, P, Q, R, S, T, V, W, Y;
V140 to A, C, D, E, F, G, H, I, K, L, M, N, P, Q, R, S, T, V, W, Y;
L147 to A, C, D, E, F, G, H, I, K, L, M, N, P, Q, R, S, T, V, W, Y;
A150 to A, C, D, E, F, G, H, I, K, L, M, N, P, Q, R, S, T, V, W, Y;
T153 to A, C, D, E, F, G, H, I, K, L, M, N, P, Q, R, S, T, V, W, Y;
Y164 to A, C, D, E, F, G, H, I, K, L, M, N, P, Q, R, S, T, V, W, Y;
D165 to A, C, D, E, F, G, H, I, K, L, M, N, P, Q, R, S, T, V, W, Y;
D167 to A, C, D, E, F, G, H, I, K, L, M, N, P, Q, R, S, T, V, W, Y;
S170 to A, C, D, E, F, G, H, I, K, L, M, N, P, Q, R, S, T, V, W, Y;
Y171 to A, C, D, E, F, G, H, I, K, L, M, N, P, Q, R, S, T, V, W, Y;
G172 to A, C, D, E, F, G, H, I, K, L, M, N, P, Q, R, S, T, V, W, Y;
A173 to A, C, D, E, F, G, H, I, K, L, M, N, P, Q, R, S, T, V, W, Y;
P174 to A, C, D, E, F, G, H, I, K, L, M, N, P, Q, R, S, T, V, W, Y;
R175 to A, C, D, E, F, G, H, I, K, L, M, N, P, Q, R, S, T, V, W, Y;
V176 to A, C, D, E, F, G, H, I, K, L, M, N, P, Q, R, S, T, V, W, Y;
G177 to A, C, D, E, F, G, H, I, K, L, M, N, P, Q, R, S, T, V, W, Y;
R179 to A, C, D, E, F, G, H, I, K, L, M, N, P, Q, R, S, T, V, W, Y;
A182 to A, C, D, E, F, G, H, I, K, L, M, N, P, Q, R, S, T, V, W, Y;
Y194 to A, C, D, E, F, G, H, I, K, L, M, N, P, Q, R, S, T, V, W, Y;
H198 to A, C, D, E, F, G, H, I, K, L, M, N, P, Q, R, S, T, V, W, Y;
N200 to A, C, D, E, F, G, H, I, K, L, M, N, P, Q, R, S, T, V, W, Y;
P207 to A, C, D, E, F, G, H, I, K, L, M, N, P, Q, R, S, T, V, W, Y;
P208 to A, C, D, E, F, G, H, I, K, L, M, N, P, Q, R, S, T, V, W, Y;
R209 to A, C, D, E, F, G, H, I, K, L, M, N, P, Q, R, S, T, V, W, Y;
G212 to A, C, D, E, F, G, H, 1, K, L, M, N, P, Q, R, S, T, V, W, Y;
S214 to A, C, D, E, F, G, H, I, K, L, M, N, P, Q, R, S, T, V, W, Y;
H215 to A, C, D, E, F, G, H, I, K, L, M, N, P, Q, R, S, T, V, W, Y;

S216 to A, C, D, E, F, G, H, 1, K, L, M, N, P, Q, R, S, T, V, W, Y;

S217 to A, C, D, E, F, G, H, I, K, L, M, N, P, Q, R, S, T, V, W, Y;

P218 to A, C, D, E, F, G, H, I, K, L, M, N, P, Q, R, S, T, V, W, Y;

E219 to A, C, D, E, F, G, H, I, K, L, M, N, P, Q, R, S, T, V, W, Y;

Y220 to A, C, D, E, F, G, H, I, K, L, M, N, P, Q, R, S, T, V, W, Y;

K223 to A, C, D, E, F, G, H, I, K, L, M, N, P, Q, R, S, T, V, W, Y;

S224 to A, C, D, E, F, G, H, I, K, L, M, N, P, Q, R, S, T, V, W, Y;

D234 to A, C, D, E, F, G, H, I, K, L, M, N, P, Q, R, S, T, V, W, Y;

I235 to A, C, D, E, F, G, H, I, K, L, M, N, P, Q, R, S, T, V, W, Y;

K237 to A, C, D, E, F, G, H, I, K, L, M, N, P, Q, R, S, T, V, W, Y;

I238 to A, C, D, E, F, G, H, I, K, L, M, N, P, Q, R, S, T, V, W, Y;

D242 to A, C, D, E, F, G, H, I, K, L, M, N, P, Q, R, S, T, V, W, Y;

A243 to A, C, D, E, F, G, H, I, K, L, M, N, P, Q, R, S, T, V, W, Y;

P250 to A, C, D, E, F, G, H, I, K, L, M, N, P, Q, R, S, T, V, W, Y;

P253 to A, C, D, E, F, G, H, I, K, L, M, N, P, Q, R, S, T, V, W, Y;

D254 to A, C, D, E, F, G, H, I, K, L, M, N, P, Q, R, S, T, V, W, Y;

I255 to A, C, D, E, F, G, H, I, K, L, M, N, P, Q, R, S, T, V, W, Y;

P256 to A, C, D, E, F, G, H, I, K, L, M, N, P, Q, R, S, T, V, W, Y;

Y261 to A, C, D, E, F, G, H, I, K, L, M, N, P, Q, R, S, T, V, W, Y,

Altered Property

The variant of the invention has one or more altered properties compared to the parent enzyme. The altered property may be, e.g., an increased thermostability, an altered pH dependence, or an altered substrate specificity.

When used in a detergent, the lipolytic enzyme may also have an improved detergence effect, particularly an improved one-cycle wash effect.

When used in baking, the lipolytic enzyme may result in a softer crumb and a better elasticity from day 0 to day 7 during storage of the baked product. Further, loaf volume and standing of the baked product may be improved. These properties may be evaluated as described in WO 0032758.

Thermostability

The thermostability can be measured at a relevant pH for the intended application using a suitable buffer. Examples of buffers and pH are: pH 10.0 (50 mM glycine buffer), pH 7.0 (50 mM HEPES Buffer) or pH 5.0 (50 mM sodium acetate as buffer).

For comparison, measurements should be made in the same buffer, at the same conditions and at the same protein concentration. Various methods can be used for measuring the thermostability:

Differential Scanning Calorimetry (DSC)

In DSC, the heating rate may be 90 degrees per hour. The sample may be purified to homogeneity, and the melting temperature ($T_M$) may be taken as an expression of the thermostability.

Residual Enzyme Activity

Alternatively, the thermostability can be determined by measuring residual lipolytic enzyme activity after incubation at selected temperatures. p-nitrophenyl ester in 10 mM Tris-HCl, pH 7.5 may be used as the substrate, as described in Giver et al., Proc. Natl. Acad. Sci. USA 95(1998)12809–12813 and Moore et al. Nat. Biotech. 14(1996) 458–467. Samples may be added periodically, or only one sample may be used with or without different additives to prevent or enhance denaturing, e.g. in a 96 well format.

CD Spectroscopy

CD spectroscopy as described e.g. in Yamaguchi et al. Protein engineering 9(1996)789–795. Typical enzyme concentration is around 1 mg/ml, Temperature between 5–80 degrees Altered Activity Substrate Specificity Compared to the parent lipolytic enzyme, the variant of the invention may have an altered substrate specificity, i.e. an altered ratio of activities towards different ester bonds in substrates. This may be used to increase a desired activity and/or decrease an undesired activity and thus decrease the ratio of an undesired activity to a desired activity.

Thus, an enzyme with increased phospholipase activity may be useful, e.g., in baking or in purification of vegetable oil. It may be desired to increase the hydrolytic activity on digalactosyl-diglyceride (DGDG) for use in baking.

It may be desired to increase the lipase activity for any industrial use where lipases are used. For use in detergents or baking it may be desired to increase the activity on long-chain ($C_{16}$–$C_{20}$) triglycerides, and it may be desired to increase the specificity for long-chain fatty acids by decreasing the ratio of activity on short-chain or medium-chain ($C_4$–$C_8$) fatty acids to the activity on long-chain fatty acids.

For use in flavor development in food products (such as cheese ripening) it may be desired to increase the lipase activity on short-chain or medium-chain ($C_4$–$C_8$) triglycerides.

For use as a phospholipase in purification of vegetable oil, it may be desired to decrease the ratio of lipase activity on long-chain ($C_{16}$–$C_{20}$) triglycerides to the phospholipase activity.

For use in detergent, the lipolytic enzyme may have an increased long-chain/short-chain specificity compared to the parent enzyme, e.g. an increased ratio of activity on long-chain (e.g. $C_{16}$–$C_{20}$) triglycerides to the activity on short-chain (e.g. $C_4$–$C_8$) triglycerides. This may be determined as the ratio of SLU with olive oil as the substrate and LU with tributyrin as substrate (methods described later in this specification).

Altered pH Dependence

The lipolytic enzyme may have an increased pH optimum or a decreased pH optimum.

The altered pH dependence may be an increased alkaline/neutral activity ratio, i.e. an increased ratio of lipase activity (e.g. lipase activity) at alkaline pH (e.g. pH 9–10) to the activity at neutral pH (around pH 7). This may be determined with tributyrine as the substrate as described later in this specification.

One-cycle Wash Effect

The one-cycle wash effect is described in WO 9707202. It may be determined by subjecting 7 lard-stained cotton swatches (9×9 cm) per beaker to a one cycle wash in a thermostated Terg-O-to-Meter (TOM), each beaker containing 1000 ml of water comprising 3.2 mM $Ca^{2+}/Mg^{2+}$ (in a ratio of 5:1) and 5 g/l of said detergent composition, pH 10, and comprising 12500 LU/l of the lipolytic enzyme, the wash treatment being carried out for 20 minutes at a temperature of 30° C., followed by rinsing for 15 minutes in running tap water and overnight line-drying at room temperature, subsequent extraction and quantification of fatty matter on the swatches by Soxhlet extraction. This may be done using Detergent Composition A or B described in WO 9707202.

Use of Variant

The variants of the invention can be used in known applications of lipolytic enzymes by analogy with the prior art, e.g.:

A variant with lipase activity can be used in the pulp and paper industry, to remove pitch or to remove ink from used paper. WO 9213130, WO 9207138, JP 2160984 A, EP 374700.

A variant with phospholipase and/or DGDGase activity can be used in the preparation of dough, bread and cakes, e.g. to increase dough stability and dough handling properties, or to improve the elasticity of the bread or cake. WO 94/04035, WO 00/32758.

A variant with phospholipase activity can be used in a process for reducing the content of phospholipid in an edible oil. U.S. Pat. No. 5,264,367 (Metallgesellschaft, Röhm); K. Dahlke & H. Buchold, INFORM, 6 (12), 1284–91 (1995); H. Buchold, Fat Sci. Technol., 95 (8), 300–304 (1993); JP-A 2-153997 (Showa Sangyo); or EP 654,527 (Metallgesellschaft, Röhm).

A variant with lysophospholipase activity can be used to improve the filterability of an aqueous solution or slurry of carbohydrate origin, e.g. starch hydrolysate, especially a wheat starch hydrolysate. EP 219,269.

A variant with phospholipase activity can be used for the preparation of lysophospholipid, e.g. lyso-lecithin (EP 870840, JP-A 10-42884, JP-A 4-135456 or JP-A 2-49593) of for the production of mayonnaise (EP 628256, EP 398666 or EP 319064).

A variant with phospholipase activity may also be used in the processing of dairy and other food products, e.g. as described in EP 567,662 (Nestlé), EP 426,211 (Unilever), EP 166,284 (Nestlé), JP-A 57-189638 (Yakult) or U.S. Pat. No. 4,119,564 (Unilever).

A variant with activity towards short-chain fatty acyl groups may be used to release free fatty acids (FFA) for flavor development in food products, e.g. in cheese ripening, e.g. as described in M. Hanson, ZFL, 41 (10), 664–666 (1990)).

A variant with phospholipase activity can be used in the leather industry. GB 2233665, EP 505920.

A variant with lipase activity may be used for removing fatty matter containing hydrophobic esters (e.g. triglycerides) during the finishing of textiles. WO 93/13256.

Use in Detergent

The variant may be used as a detergent additive, e.g. at a concentration (expressed as pure enzyme protein) of 0.001–10 (e.g. 0.01–1) mg per gram of detergent or 0.001–100 (e.g. 0.01–10) mg per liter of wash liquor. In detergents, the variant may have a high activity on long-chain triglycerides ($C_{16}$–$C_{20}$) to improve the removal of fatty soiling. The variant may have phospholipase activity. The variant may have low activity towards short-chain ($C_4$–$C_8$) fatty acids in triglycerides. WO 97/04079, WO 97/07202, WO 97/41212, WO 98/08939 and WO 97/43375.

The lipolytic enzyme of the invention may be used in a detergent composition. It may be included in the detergent composition in the form of a non-dusting granulate, a stabilized liquid, or a protected enzyme. Non-dusting granulates may be produced, e.g., as disclosed in U.S. Pat. No. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods.

The detergent composition may be in any convenient form, e.g. as powder, granules, paste or liquid. A liquid detergent may be aqueous, typically containing up to 70% water and 0–30% organic solvent, or non-aqueous.

The detergent composition comprises one or more surfactants, each of which may be anionic, nonionic, cationic, or zwitterionic. The detergent will usually contain 0–50% of anionic (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfon-ate (NOBS). Alternatively, the bleaching system may comprise peroxyacids of, e.g., the amide, imide, or sulfone type.

The pH (measured in aqueous solution at use concentration) will usually be neutral or alkaline, e.g. in the range of 7–11.

Further, the detergent may be a dishwashing detergent with surfactant typically containing 0–90% of non-ionic surfactant such as low- to non-foaming ethoxylated propoxylated straight-chain alcohols.

Nomenclature for Amino Acid Substitutions

The nomenclature used herein for defining amino acid substitutions uses the single-letter code, as described in WO 92/05249.

Thus, D27N indicates substitution of D in position 27 with N. D27N/R indicates a substitution of D27 with N or R. L227X indicates a substitution of L227 with any other amino acid. D27N+D111A indicates a combination of the two substitutions.

Homology and Alignment

For purposes of the present invention, the degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–45), using GAP with the following settings for polypeptide sequence comparison: GAP creation penalty of 3.0 and GAP extension penalty of 0.1.

In the present invention, corresponding (or homologous) positions in the lipase sequences of *Rhizomucor miehei* (rhimi), *Rhizopus delemar* (rhidl), *Thermomyces lanuginosus* (former; *Humicola lanuginosa*) (SP400), *Penicillium camembertii* (Pcl) and *Fusarium oxysporum* (FoLnp11), are defined by the alignment shown in FIG. 1 of WO 00/32758.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–45). The following settings are used for polypeptide sequence comparison: GAP creation penalty of 3.0 and GAP extension penalty of 0.1.

Procedure for Obtaining Thermostable Variants

Thermostable variants of a given parent lipolytic enzyme can be obtained by the following standard procedure:
ξ Mutagenesis (error-prone, doped oligo, spiked oligo)
ξ Primary Screening
ξ Identification of more temperature stable mutants
ξ Maintenance (glycerol culture, LB-Amp plates, Mini-Prep)
ξ Streaking out on another assay plate—secondary screening (1 degree higher then primary screening)
ξ DNA Sequencing
ξ Transformation in Aspergillus
ξ Cultivation in 100 ml scale, purification, DSC Primary Screening Assay The following assay method is used to screen lipolytic enzyme variants and identify variants with improved thermostability.

*E. coli* cells harboring variants of a lipolytic enzyme gene are prepared, e.g. by error-prone PCR, random mutagenesis or localized random mutagenesis or by a combination of beneficial mutants and saturation mutagenesis.

The assay is performed with filters on top of a LB agar plate. *E. coli* cells are grown on cellulose acetate filters supplied with nutrients from the LB agar plate and under the selection pressure of ampicillin supplied with the LB agar. Proteins including the desired enzyme are collected on a nitrocellulose filter between LB agar and cellulose acetate filter. This nitrocellulose filter is incubated in a buffer of desired pH (generally 6.0) and at the desired temperature for 15 minutes (e. g. 78 degrees for the *T. lanuginosus* lipase). After quenching the filters in ice-water, the residual lipase activity is determined through the cleavage of indole acetate and the subsequent coloration of the reaction product with nitro-blue tetrazolium chloride as described by Kynclova, E et al. (Journal of Molecular Recognition 8 (1995)139–145).

The heat treatment applied is adjusted so that the parent generation is slightly active, approximately 5–10% compared to samples incubated at room temperature. This facilitates the identification of beneficial mutants.

---

The invention claimed is:

1. A variant of a fungal parent lipolytic enzyme, which comprises one or more of the following amino acid substitutions:

A150 to G;
I238 to V and;
P250 to N, Q or V;

wherein (a) each position corresponds to the position of the amino acid sequence of SEQ ID NO: 1;
(b) the variant has lipolytic activity; and
(c) the variant has at least 90% homology with SEQ ID NO: 1 determined using the GAP computer program provided in the GCG program package (Program Manual for the Wisconsin Package, Version 8, August 1994, Genetics Computer Group, 575 Science Drive, Madison, Wis., USA 53711) with the following settings for polypeptide sequence comparison: GAP creation penalty of 3.0 and GAP extension penalty of 0.1.

2. The variant of claim 1, wherein the variant has at least 95% homology with SEQ ID NO:1.

3. The variant of claim 1, wherein the variant has a total of no more than 10 substitutions as compared to SEQ ID NO:1.

4. The variant of claim 1, wherein the variant has a total of no more than 5 substitutions as compared to SEQ ID NO:1.

5. The variant of claim 1, wherein the parent lipolytic enzyme is a *Thermomyces lanuginosus* lipase.

6. The variant of claim 1, wherein the parent lipolytic enzyme is the lipase shown in SEQ ID NO: 1.

7. The variant of claim 1, which comprises A150 to G.

8. The variant of claim 1, which comprises I238 to V.

9. The variant of claim 1, which comprises P250 to N.

10. The variant of claim 1, which comprises P250 to Q.

11. The variant of claim 1, which composes P250 to V.

12. The variant of claim 1, further comprising one or more of the following substitutions:

Q15 to A, C, D, E, F, G, I, K, L, M, N, P, R, S, T, V, W, Y;
Y16 to A, C, D, E, F, G, H, I, K, L, M, N, P, Q, R, S, T, V, W;
A18 to C, D, E, F, G, H, I, K, L, M, N, P, Q, R, S, T, V, W, Y;
A19 to C, D, E, F, G, H, I, K, L, M, N, Q, R, S, V, W, Y;
A20 to C, D, E, F, G, H, I, K, L, M, N, Q, R, S, T, V, W, Y;
N25 to A, C, D, E, F, G, H, I, K, L, M, P, Q, R, S, T, V, W, Y;
N26 to A, D, E, F, G, H, I, K, L, M, P, Q, R, S, T, V, W, Y;
E43 to A, C, D, F, G, H, I, K, L, M, N, R, S, T, V, W, Y;
V44 to A, C, D, E, F, G, H, I, K, L, M, N, Q, R, S, T, W, Y;
K46 to A, C, D, E, F, G, H, I, L, M, N, Q, S, T, V, W, Y;
A47 to C, D, E, F, G, H, I, K, L, M, N, P, Q, R, S, T, W, Y;
A49 to C, D, E, F, G, H, I, K, L, M, N, Q, R, S, V, W, Y;
L52 to A, C, D, E, F, G, H, I, K, M, N, P, Q, R, S, T, V, W, Y;
Y53 to A, D, E, F, G, H, I, K, L, M, N, P, Q, R, S, T, V, W;
S54 to A, C, D, E, F, G, H, I, K, L, M, N, Q, R, T, V, W, Y;
G65 to A, C, D, E, F, H, I, K, L, M, N, P, Q, R, S, T, V, W, Y;
L67 to A, C, D, E, F, G, H, I, K, M, N, Q, R, S, T, V, W, Y;
A68 to C, D, E, F, G, H, I, K, L, M, N, P, Q, R, S, T, V, W, Y;
L69 to A, C, D, E, F, G, H, I, K, M, N, P, Q, S, T, V, W, Y;
T72 to A, C, D, E, F, G, H, I, L, M, N, P, Q, R, S, V, W, Y;
K74 to A, C, D, E, F, G, H, I, L, M, N, P, Q, R, S, T, V, W, Y;

L75 to A, C, D, E, F, G, H, I, K, M, N, P, Q, R, S, T, V, W, Y;
V77 to A, C, D, E, F, G, H, I, K, L, M, N, P, Q, R, S, T, W, Y;
S79 to A, C, D, E, F, G, H, I, K, L, M, N, P, Q, R, T, V, W, Y;
R81 to A, D, E, F, G, H, I, K, L, M, N, P, Q, S, T, V, W, Y;
S83 to A, C, D, E, F, G, H, I, K, L, M, N, Q, R, V, W, Y;
S85 to A, D, E, G, H, I, L, M, N, Q, V, W, Y;
W89 to A, C, D, E, F, H, I, K, L, M, N, P, Q, R, S, T, V, Y;
L97 to A, C, D, E, F, G, H, I, K, N, P, R, S, T, W, Y;
K98 to A, C, G, H, L, M, N, P, Q, S, T, V, W, Y;
E99 to C, F, G, I, M, P, W, Y;
G106 to A, C, D, E, F, H, I, K, L, M, N, P, Q, R, T, V, W, Y;
C107 to A, D, E, F, G, H, I, K, L, M, N, P, Q, R, S, T, V, W, Y;
R108 to A, C, D, E, F, G, H, I, K, L, M, N, P, Q, S, T, V, Y;
G109 to A, C, D, E, F, H, I, K, L, M, N, P, Q, R, S, T, W, Y;
T123 to A, C, D, E, F, G, H, I, K, L, M, N, P, Q, R, S, V, W, Y;
L124 to A, C, D, E, F, G, H, I, K, M, N, P, Q, R, T, V, W, Y;
K127 to A, D, E, F, G, H, I, L, M, N, P, Q, R, S, T, V, W, Y;
E129 to A, C, D, F, G, H, I, L, M, N, P, Q, R, S, T, V, W, Y;
A131 to C, D, E, F, G, H, I, K, L, M, N, P, Q, R, S, T, V, W, Y;
V132 to A, C, D, E, F, G, H, I, K, L, N, P, Q, R, S, T, W, Y;
Y138 to A, C, D, E, F, G, H, I, K, L, M, N, P, Q, R, S, T, V, W;
V140 to A, C, D, E, F, G, H, I, K, L, M, N, P, R, S, T, W, Y;
L147 to A, C, D, E, F, G, H, I, K, M, N, P, Q, R, S, T, V, W, Y;
T153 to A, C, D, E, F, G, H, I, K, L, M, N, P, Q, R, S, V, W, Y;
Y164 to A, C, D, E, F, G, H, I, K, L, M, N, P, Q, R, S, T, V, W;
D165 to A, C, E, F, G, H, I, K, L, M, N, Q, S, T, V, W, Y;
D167 to A, C, E, F, H, I, L, M, N, P, Q, S, T, V, W, Y;
S170 to A, C, D, E, F, G, H, I, K, L, M, N, Q, R, T, V, W, Y;
Y171 to A, C, D, E, F, G, H, I, K, L, M, N, P, Q, R, S, T, V, W;
G172 to A, C, D, E, F, H, I, K, L, M, N, P, Q, R, S, T, V, W, Y;
A173 to C, D, E, F, G, H, I, K, L, M, N, Q, R, S, T, V, W, Y;
P174 to A, C, D, E, F, G, H, I, K, L, M, N, Q, R, S, T, V, W, Y;
R175 to A, C, D, E, F, G, H, I, K, L, M, N, Q, S, T, V, W, Y;
V176 to A, C, D, E, F, G, H, I, K, L, M, N, P, Q, R, S, T, W, Y;
G177 to A, C, D, E, F, H, I, K, L, M, N, P, Q, S, T, V, W, Y;
R179 to A, C, D, E, F, G, H, I, K, L, M, N, P, Q, S, T, V, W, Y;
A182 to C, D, E, F, G, H, I, K, L, M, N, P, Q, R, S, T, V, W, Y;
Y194 to A, C, D, E, F, G, H, I, K L, M, N, P, Q, R, S, T, V, W;
H198 to A, C, D, E, F, G, I, K, L, M, N, P, Q, R, S, T, V, W, Y;
N200 to A, C, D, E, F, G, H, I, K, L, M, P, Q, S, T, V, W, Y;
P207 to A, C, D, E, F, G, H, I, K, L, M, N, Q, R, S, T, V, W, Y;
P208 to A, C, D, E, F, G, H, I, K, L, M, N, Q, R, S, T, V, W, Y;
R209 to C, D, F, G, H, I, K, L, M, N, Q, T, V, W, Y;
G212 to A, C, D, E, F, H, I, K, L, M, N, P, Q, R, S, T, V, W, Y;
S214 to A, C, D, E, F, G, H, I, K, L, M, N, P, Q, R, T, V, W, Y;
H215 to A, C, D, E, F, G, I, K, L, M, N, P, Q, R, S, T, V, W, Y;
S216 to A, C, D, E, F, G, H, I, K, L, M, N, Q, R, T, V, W, Y;
S217 to A, C, D, E, F, G, H, I, K, L, M, N, P, Q, R, T, V, W, Y;
P218 to A, C, D, E, F, G, H, I, K, L, M, N, Q, R, S, T, V, W, Y;
E219 to C, D, F, H, I, M, P, W, Y;
Y220 to A, C, D, E, F, G, H, I, K, L, M, N, P, Q, R, S, T, V, W;
K223 to A, C, D, E, F, G, H, I, L, M, N, Q, S, T, V, W, Y;
S224 to A, C, D, E, F, G, H, I, K, L, M, N, Q, T, V, W, Y;
D234 to C, E, F, H, I, M, W;
I235 to A, C, D, E, F, G, H, K, L, M, N, P, Q, R, S, T, V, W, Y;
K237 to A, C, D, E, F, G, H, I, L, N, P, Q, S, T, V, W, Y;
D242 to C, E, F, G, H, I, M, P, W, Y;
A243 to C, D, E, F, G, H, I, K, L, M, N, P, Q, R, S, V, W, Y;
P253 to A, C, D, E, F, G, H, I, K, L, M, N, Q, S, T, V, W, Y;
D254 to C, E, F, H, I, M, P, Y; and
Y261 to A, C, E, F, G, H, L, M, N, P, Q, R, S, T, V.

13. The variant of claim 1, wherein the fungal parent lipolytic enzyme is a lipase.

14. The variant of claim 1, which variant has at least 90% homology with SEQ ID NO: 1 as determined using the GAP computer program provided in the GCG program package (Program Manual for the Wisconsin Package, Version 8, August 1994, Genetics Computer Group, 575 Science Drive. Madison, Wis., USA 53711) with the following settings for polypeptide sequence comparison: GAP creation penalty of 3.0 and GAP extension penalty of 0.1 and comprises A150 to G.

15. The variant of claim 1, which variant has at least 90% homology with SEQ ID NO: 1 as determined using the GAP computer program provided in the GCG program package (Program Manual for the Wisconsin Package, Version 8, August 1994, Genetics Computer Group, 575 Science Drive, Madison, Wis., USA 53711) with the following settings for polypeptide sequence comparison: GAP creation penalty of 3.0 and GAP extension penalty of 0.1 and comprises I238 to V.

16. The variant of claim 1, which variant has at least 90% homology with SEQ ID NO: 1 as determined using the GAP computer program provided in the GCG program package (Program Manual for the Wisconsin Package, Version 8, August 1994. Genetics Computer Group, 575 Science Drive, Madison, Wis. USA 53711) with the following settings for polypeptide sequence comparison: GAP creation penalty of 3.0 and GAP extension penalty of 0.1 and comprises P250 to N.

17. The variant of claim 1, which variant has at least 90% homology with SEQ ID NO: 1 as determined using the GAP computer program provided in the GCG program package (Program Manual for the Wisconsin Package, Version 8. August 1994, Genetics Computer Group. 575 Science Drive, Madison, Wis., USA 53711) with the following settings for polypeptide sequence comparison: GAP creation penalty of 3.0 and GAP extension penalty of 0.1 and comprises P250 to Q.

18. The variant of claim 1, which variant has at least 90% homology with SEQ ID NO: 1 as determined using the GAP computer program provided in the GCG program package (Program Manual for the Wisconsin Package, Version 8 August 1994, Genetics Computer Group, 575 Science Drive, Madison, Wis., USA 53711) with the following settings for polypeptide sequence comparison: GAP creation penalty of 3.0 and GAP extension penalty of 0.1 and comprises P250 to V.

19. The variant of claim 1, which variant has at least 95% homology with SEQ ID NO: 1 as determined using the GAP computer program provided in the GCG program package (Program Manual for the Wisconsin Package, Version 8, August 1994, Genetics Computer Group. 575 Science Drive, Madison, Wis., USA 53711) with the following settings for polypeptide sequence comparison: GAP creation penalty of 3.0 and GAP extension penalty of 0.1 and comprises A150 to G.

20. The variant of claim 1, which variant has at least 95% homology with SEQ ID NO: 1 as determined using the GAP computer program provided in the GCG program package (Program Manual for the Wisconsin Package. Version 8. August 1994. Genetics Computer Group, 575 Science Drive, Madison, Wis., USA 53711) with the following settings for polypeptide sequence comparison: GAP creation penalty of 3.0 and GAP extension penalty of 0.1 and comprises 1238 to V.

21. The variant of claim 1, which variant has at least 95% homology with SEQ ID NO: 1 as determined using the GAP computer program provided in the GCG program package (Program Manual for the Wisconsin Package, Version 8, August 1994, Genetics Computer Group, 575 Science Drive, Madison, Wis., USA 53711) with the following settings for polypeptide sequence comparison: GAP creation penalty of 30 and GAP extension penalty of 0.1 and comprises P250 to N.

22. The variant of claim 1, which variant has at least 95% homology with SEQ ID NO: 1 as determined using the GAP computer program provided in the GCG program package (Program Manual for the Wisconsin Package, Version 8, August 1994, Genetics Computer Group, 575 Science Drive, Madison, Wis., USA 53711) with the following settings for polypeptide sequence comparison: GAP creation penalty of 3.0 and GAP extension penalty of 0.1 and comprises P250 to Q.

23. The variant of claim 1, which variant has at least 95% homology with SEQ ID NO: 1 as determined using the GAP computer program provided in the GCG program package (Program Manual for the Wisconsin Package. Version 8, August 1994, Genetics Computer Group, 575 Science Drive, Madison, Wis., USA 53711) with the following settings for polypeptide sequence comparison: GAP creation penalty of 3.0 and GAP extension penalty of 0.1 and comprises P250 to V.

* * * * *